United States Patent [19]
Hessel et al.

[11] Patent Number: 5,945,107
[45] Date of Patent: Aug. 31, 1999

[54] COMPOSITIONS AND METHODS FOR WEIGHT REDUCTION

[75] Inventors: Lasse Lief Hessel; Jorgen Scherning Lundsgaard, both of Svendborg, Denmark

[73] Assignee: Natural Medio Tech A/S, Albertslund, Denmark

[21] Appl. No.: 09/206,081

[22] Filed: Dec. 4, 1998

[51] Int. Cl.$^6$ .................................................. A61K 35/78
[52] U.S. Cl. .......................................................... 424/195.1
[58] Field of Search ........................................... 424/195.1

[56] References Cited

U.S. PATENT DOCUMENTS

| | | | |
|---|---|---|---|
| 4,861,594 | 8/1989 | Subbiah | 424/195.1 |
| 5,273,754 | 12/1993 | Mann | 424/440 |
| 5,798,101 | 8/1998 | Haveson | 424/195.1 |

*Primary Examiner*—Raymond J. Henley, III
*Attorney, Agent, or Firm*—Law Offices of Jane Massey Licata

[57] ABSTRACT

Compositions containing a combination of selected herbal plant extracts that inhibit gastric emptying time and increase metabolic rate are provided which are useful in reducing weight in patients.

3 Claims, No Drawings

COMPOSITIONS AND METHODS FOR WEIGHT REDUCTION

BACKGROUND OF THE INVENTION

Obesity is a condition that affects millions of Americans. Recent statistics show that when obesity is defined as a 20% excess over desirable weight, 20–30% of adult men and 30–40% of adult women are obese. Even mild obesity increases the risk for premature death, diabetes, hypertension, atherosclerosis, gallbladder disease, and even some forms of cancer (Olefsky, J. M. 1994, *Harrison's Principles of Internal Medicine,* 446–452). Therefore, effective methods for weight reduction are constantly being sought.

Although there are many different treatment regimens in use today that can produce a short term or temporary weight loss, most are associated with a rapid increase in weight once treatment is terminated. Caloric restriction is the main goal of most weight reduction treatment regimens. The basic principle is that if intake of food is less than energy expenditure, stored calories will be consumed, mainly in the form of fat. However, once the diet regimen is broken, weight is quickly regained.

Other treatment regimens are based on the principle of increasing metabolism. By increasing metabolism, calories are burned thereby decreasing body weight. However, these treatments often have side effects, particularly those involving use of non-prescription and prescription drug products. Further, these treatments also often result in rapid weight increases once treatment is terminated, unless modification of behavior that led to weight gain is undertaken. In the case of nutritional supplement regimens, poor taste is often a problem despite addition of taste-improving substances to the product.

Weight reduction has also been attempted using surgical intervention wherein the size of the stomach is reduced so that a feeling of gastric fullness is produced, resulting in a decrease in appetite and food intake. One such method is placement of a mechanical device such as an inflatable balloon into the stomach. However, such invasive methods are not routinely used.

The use of herbal plant extracts to control weight has also been described. For example, the herb Guarana (*Paullinia cupana, P. sorbolis*) which contains a high concentration of the active ingredient caffeine has been incorporated into slimming products (Hurel, J.-P., 1993, FR 2 712 191-A1). Caffeine is recognized to have pharmacological activity as a central nervous system stimulant and is a major constituent in many weight-reducing products for its ability to increase metabolic rate. However, use of such a product alone has only a temporary effect, with weight gain seen immediately upon cessation of treatment. Similarly, Prunet (FR 2 687 548 A1) describes the use of Guarana as a nutritional supplement in short term weight reduction. Finally, Primez (Belgium Patent 100593A7) describes a phyto-active mixture referred to as Lycopodium which contains Guarana and other plant extracts including *Scillia maritime, Ephedra vulgaris,* and *Betula alba* which may be ingested, applied as a cream or lotion, or injected to produce weight loss. It is suggested that administration of Lycopodium slows gastric draining while improving intestinal transit and evacuation of the intestines. However, no clinical data is provided to support this suggestion.

It has now been found that a combination of selected herbal extracts wherein at least one of the extracts contains caffeine and at least one of the extracts controls gastric emptying is capable of producing weight loss.

SUMMARY OF THE INVENTION

An object of the present invention is to provide a composition comprising a combination of selected herbal extracts that produces weight loss in a patient through inhibition of gastric emptying and an increase in metabolic rate in the patient.

Another object of the present invention is to provide a method of reducing weight in patients which comprises administering to the patient a composition comprising a combination of selected herbal extracts that inhibits gastric emptying and increases metabolic rate in the patient.

DETAILED DESCRIPTION OF THE INVENTION

The periodic discharge of food from the stomach into the small intestine, also referred to as gastric emptying, is caused by contraction of the muscles in the wall of the stomach. These muscles are innervated by the cranial vagus nerves, which stimulate contraction of the gastric muscles and allow sphincter between the stomach and the duodenum to open. The present invention relates to a composition comprising a combination of selected herbal extracts wherein at least one of the herbal extracts inhibits gastric emptying. Because nutritional uptake through the mucosal lining of the stomach is extremely low, the extended retention period in the stomach of food resulting from these compositions does not have any discernable effect on the eventual uptake of nutrients. However, inhibition of gastric emptying results in a decreased appetite thereby decreasing food intake. The compositions of the present invention further comprise at least one herbal extract capable of modifying metabolic rate through the presence of significant concentrations of caffeine. Increasing the metabolic rate of a patient while inhibiting gastric emptying in the patient by administering a composition of the present invention results in weight loss. Active ingredients extracted from the plants are used as a natural nutritional supplement in such a way to control the uptake of nutrients by delaying gastric emptying. At the same time plant extracts are incorporated which are known to promote weight loss by increasing metabolism. The composition of the present invention thus provides a combination of selected herbal extracts which has been shown to be effective in producing weight loss in clinical studies.

Herbal plant extracts that have been assessed and found to be suitable for selection and incorporation into a composition of the present invention for achieving a controlled and durable weight loss include Buchu (*Barosma betulina, B. crenulata, B. serratifolia*), Vervain (*Verbena officinales, V. jamaicensis, V. lappulacae, V. hesitate, V. urticifolia, V. Sinuata*), Damiana (*Tumera diffusa* var. *aphrodisiaca, T. opifera, T. ulmifoliei*), Guarana (*Paullinia cupana, P. sorbalis*), Paraguay (*Ilex paraguarensis, I. vomitora, I. Dahoon*), Kola (*Cola nitida, C. vera*), and Ginseng (*Panax ginseng, P. quinquefolius* L.). The active ingredients of each herb are listed in Table 1:

TABLE 1

Active Ingredients of Selected Herbs

| Herb | Active Ingredient(s) |
|---|---|
| Buchu | volatile oil of buchu camphor, diosphenol |
| Vervain | verbanaline (glycoside, adenosine, essential oils tannin, livertin, emulin |
| Damiana | ethers, terpenes (a-pinene, cineol, p-cymol, sesquiterpenes), resin, bitter pineapple, tannin, caoutchouc, albuminoids, starch, arbutin |
| Guarana | caffeine, other xanthines (tetramethylxanthine, theobromine, theophylline, tannin) |
| Paraguay | caffeine |
| Kola | caffeine |
| Ginseng | triterpenoid saponin |

As will be obvious to those of skill in the art, other herbal extracts having these active ingredients can also be selected for use in a composition of the present invention. Herbal extracts for combination into a composition of the present invention are obtained in accordance with methods well known and routine to those of skill in the art.

A composition of the present invention comprising a combination of selected herbal extracts was administered to patients in a double blind controlled clinical trial. The combination tested included Guarana, Damiana, and Paraguay. Guarana is a dough from the seeds of *Paullinia sorbolis*, which grows in Brazil and Venezuela. It contains 3–6% caffeine, 5–8.5% tannin, 7.8% resins, 2–3% fat, 0.06% saponin, 5–6% starch, and 1.5% coloring agents. Paraguay is an extract of *Ilex paraguensis* which grows in Brazil, Argentina, and Paraguay. It contains 1–1.5% caffeine, 4–10% tannin, and 3% resins and fat. Damiana is obtained form the leaves of the plant *Turnera diffusa* var. *aphrodisiacs* from California, Mexico, Brazil, and Bolivia and contains ethereal oils, resins, and tannin. These extracts were obtained as powders. The components were mixed and prepared as capsules. Each capsule contained 95 mg Guarana, 112 mg Paraguay, and 36 mg Damiana extract. The subjects for the study were 20 otherwise healthy subjects, complaining of light-moderate overweight with a body mass index between 25 and 30 $kg/m^2$. None of the subjects were taking any drug or dietary supplement at the time of the study. All were briefed on the protocol and gave consent to the trial.

In this double blind placebo controlled trial, the subjects were randomized into two groups A and B. Group A was supplied with test capsules and group B with placebo (water coated capsules containing lactose) for 20 days. The participants took three meals a day and were instructed to take 2 capsules with a large glass of water (250 ml) from 10–15 minutes before each meal. Using a stopwatch, each subject then recorded the time elapsing to perception of gastric fullness. Subjects also were asked to note any side effects. Three days after the end of the first 20 day trial, the procedure was repeated with the test capsules now being given to the group B subjects and the placebo capsules to group A subjects. All subjects completed the test.

The subjects in group B, receiving the placebo capsules in the first period reported an average time for perception of fullness of 60 minutes (range 55–65 minutes). In the second period, when taking the test combination product, the average time for perception of fullness in this same group was 36 minutes (range 33–41 minutes). These average values were statistically different ($p<0.01$). Therefore, the study showed that treatment with the herbal extract combination produced statistically significant decreases in the time to perception of fullness.

The rate of gastric emptying was assessed by scintigraphy. Three volunteer male subjects with no gastrointestinal illness or intake of medicinal drugs took part in the study. They were given a meal consisting of 18 g peas, 100 g dried potatoes, and 200 ml of water containing 16–20 Mbc 113 Indium-DPTA. The subjects were fasting before the test and the meal was consumed in five minutes. The test was conducted with the subjects in a semi-upright position with a gamma camera placed in front. The time course of radioactivity in the stomach was determined by measuring the radioactivity in an appropriate region of interest every minute over 90 minutes. The test as repeated after each subject had taken three capsules of the drug combination three times daily and three capsules having been mixed with the food. Results showed that the rate of gastric emptying was significantly decreased in the three subjects after taking the herbal extract combination product. Halving times of gastric emptying were 49, 31, and 32 minutes after taking the test product and 61, 50, and 49 minutes, respectively, after taking the placebo.

Ultrasound examination of the stomach was also employed using a 3.5 MHz curved array transducer and an Aloka 630 standard unit employing a modification of the techniques by Holt et al. (Holt, S. et al., 1980, *Gut*, 1:597–601) and Bateman and Whittingham (Bateman, D. N. and T. A. Whittingham, 1982, *Gut*, 23:524–527). Continuous scans were performed switching the transducer between two alternate projections, one oblique upward view with the transducer positioned under the left curvature allowing the gastric fundus, corpus, and antrum to be inspected or a transverse view across the epigastrium with a slight upward direction viewing the antrum pylorus and the duodenal bulb. All examinations were recorded on videotape and still pictures were taken every five minutes. This technique was used in a further double-blind crossover study on 7 healthy normal volunteers with no history of gastrointestinal diseases. Each volunteer had 2 to 8 examinations with the test capsules or placebo capsules (lactose), followed by 20 ml of apple juice and 15 minutes later with 400 ml of apple juice. The projections gave clear visual estimation of the volume of the stomach. Gastric emptying time (GET) was defined as the elapsed time between ingestion of the 400 ml of apple juice and the time when the fundus and corpus of the stomas were completely empty. The results were noted immediately and controlled by playback of the videotapes. After termination of the study the codes were broken and GET values were compared by an independent analyst. The results showed that there was a considerable variation among the subjects and within the same subject. However, even with this variability, a delaying effect on gastric emptying was associated with administration of the herbal extract combination product, an effect that was evident in all seven subjects and is shown in Table 2.

TABLE 2

Results of the Ultrasound Study:
Comparison of Gastric Emptying Time (GET)

| Subject | Placebo GET (minutes) | Herbal Extract GET (minutes) |
|---|---|---|
| A | 37.0 | 63.5 |
| B | 47.5 | 70.0 |
| E | 45.5 | 80.0 |
| M | 29.0 | 44.5 |
| H | 31.0 | 46.0 |
| J | 34.0 | 39.0 |
| T | 44.0 | 60.0 |
| Mean Value | 31.8 | 57.6 |

The effect on body weight of 10 days treatment with the test compound and placebo was recorded in a double blind pilot study of 44 healthy subjects was also determined. None of the subjects took any drugs and none were on a specific diet. The patients were instructed to take three capsules (test compounds or placebo) with a large glass of water 15 minutes before main meals and also to take care to not change their normal food habits. They also were asked to note side effects. The subjects were weighed before and after the period of 10 days. Twenty-two patients with a BMI range 25.1 to 29.5 took the test capsules and 22 patients with a BMI of 24.9 to 29.0 received the placebo. Results showed that of the 22 subjects who received the placebo, there was a mean decrease in body weight of 0.3 kg (SEM=0.03) while in the 22 subjects who received the herbal extract product, there was a mean decrease of 0.8 kg (SEM=0.05).

The effect on body weight of 45 days of treatment with the herb combination and placebo was also studied in a double blind randomized crossover study of 47 patients. These subjects were healthy but overweight (BMI range 25.8 to 30.4). They did not take any medicinal drug or diet before or during the study. All 47 were between the ages of 20 and 60 years of age and gave full consent. In the study, the 24 subjects in group A received the test capsules in the first period. This group showed a mean decrease in body weight of 5.1 kg (SEM=0.5) while taking the herbal extract product. In contrast, the placebo group in the first period had a mean decrease in body weight of only 0.5 kg (SEM=0.08).

A recording of weight maintenance over 12 months after an initial weight loss was made to assess the long term effectiveness of the treatment. Twenty-two of the subjects from the various studies above who had lost an average of 3.6 kg were invited to take part. Each subject received a month's supply of the test drug each month they returned to the study center for weight measurement.

No side effects were noted in any of the clinical tests. The results of these experiments demonstrate the effectiveness of the herbal extract combination in weight reduction in humans.

What is claimed is:

1. A composition which produces weight loss in a patient comprising a combination of selected herbal extracts wherein said combination comprises at least one herbal extract capable of inhibiting gastric emptying and one herbal extract which increases metabolic rate in a patient.

2. The composition of claim 1 wherein the combination of selected herbal extracts comprises Guarana, Damiana, and Paraguay.

3. A method of reducing weight in a patient comprising administering to a patient a composition of claim 1 so that gastric emptying is inhibited and metabolic rate is increased in the patient.

* * * * *

UNITED STATES PATENT AND TRADEMARK OFFICE
CERTIFICATE OF CORRECTION

PATENT NO. : 5,945,107
DATED : August 31, 1999
INVENTOR(S) : Hessel et al.

It is certified that error appears in the above-indentified patent and that said Letters Patent is hereby corrected as shown below:

On the title page:

Item [73]: Assignee, please delete "Natural Medio" and insert therefor --Natural Medico--.

Signed and Sealed this

Eighth Day of August, 2000

Attest:

Q. TODD DICKINSON

*Attesting Officer*      *Director of Patents and Trademarks*

UNITED STATES PATENT AND TRADEMARK OFFICE
CERTIFICATE OF CORRECTION

PATENT NO. : 5,945,107
DATED : August 31, 1999
INVENTOR(S) : Hessel et al.

It is certified that error appears in the above-identified patent and that said Letters Patent is hereby corrected as shown below:

Title page,
Insert Item:
-- Related U.S. Application Data
[60] Provisional application No. 60/067,706 filed Dec. 8, 1997 --.

Signed and Sealed this

Fourth Day of January, 2005

JON W. DUDAS
*Director of the United States Patent and Trademark Office*

(12) EX PARTE REEXAMINATION CERTIFICATE (7198th)
United States Patent
Hessel et al.

(10) Number: US 5,945,107 C1
(45) Certificate Issued: Dec. 1, 2009

(54) COMPOSITIONS AND METHODS FOR WEIGHT REDUCTION

(75) Inventors: Lasse Lief Hessel, Svendborg (DK); Jorgen Scherning Lundsgaard, Svendborg (DK)

(73) Assignee: Natures Remedies Ltd., Amersham Buckinghamshire (GB)

Reexamination Request:
No. 90/007,785, Oct. 31, 2005

Reexamination Certificate for:
Patent No.: 5,945,107
Issued: Aug. 31, 1999
Appl. No.: 09/206,081
Filed: Dec. 4, 1998

Certificate of Correction issued Aug. 8, 2000.

Certificate of Correction issued Jan. 4, 2005.

Related U.S. Application Data
(60) Provisional application No. 60/067,706, filed on Dec. 8, 1997.

(51) Int. Cl.
*A61K 35/78* (2006.01)
*A61K 36/00* (2006.01)
*A01N 65/00* (2006.01)

(52) U.S. Cl. ...................................... 424/728; 424/725
(58) Field of Classification Search ............... 424/195.1, 424/440
See application file for complete search history.

(56) References Cited

FOREIGN PATENT DOCUMENTS

| BE | 1 005 963 | 4/1994 |
| FR | 2 687 548 | 8/1993 |
| FR | 2 712 191 | 5/1995 |
| WO | PCT/EP98/07810 | 6/1999 |

OTHER PUBLICATIONS

Product packaging: Minus Kalorien Rotationsdiat (German/English) [Minus–Cal] Europe distribution: 1986.*
Advertisement for Tab–Let (Danish/English); Denmark's Big Coupon Catalog, Jun. 1996.*
A.F. Hill: Economic Botany: A Textbook of Useful Plants and Plant Products (McGraw Hill Book Inc. $2_{nd}$ Ed. 1952) pp. 468 and 479–481.*
K.J. Acheson, et al.; Caffeine and coffee: their influence on metabolic rate and substrate utilization in normal weight and obese individuals; The American Journal of Clinical Nutrition, 33, 989–997, May 1980.
A.G. Dulloo, et al.; Normal caffeine consumption: influence on thermogenesis and daily energy expenditure in lean and postobese human volunteers; American Journal of Clinical Nutrition, 49, 44–50, 1989.
K. Jonderko, et al.; Effect of anti–obesity drugs promoting energy expenditure, yohimbine and ephedrine, on gastric emptying in obese patients; Aliment. Pharmacol. Therap., 5, pp. 413–418, 1991.
Edited by R.G. Todd; Martindale: Extra Pharmacopoeia; The Pharmaceutical Press, ed. 25, pp. 252, 1509, 1518, 1526, 1533, 1967.
K. Bempong, et al.; Dissolution an absorption of caffeine from guarana; J. Pharm. Pharmacol. 44: 769–771, 1992.
D.B. Mowrey; Fat management: The Thermogenic Factor; Victory Publications, pp. 37–38, 51, 243–244, 246–251, 1994.
J. Lust; The Herb Book; Bantam Books, 1974, pp. 136137, 186, 229, 247–248, 270, 522 526.
D. B. Mowrey; The Scientific Validation of Herbal Medicine; Publishing, Inc., p. 152, 1986.
Product packaging: Minus Kalorien Rotationsdiät (German, English [Minus–Cal]); Distributed in Europe at least as early as 1986.
C. Geissler, et al., Double–Blind Trial of Herbal Slimming Pill; Lancet, 2(8504), p. 461, 1986.
Application to the scientific–ethical committee for project entitled, The effect of Medi–Tab capsules on the ventricular emptying time, and investigation protocol and project description (Danish, English); Scientific–Ethical Committee of Copenhagen State, Reference No. KA 96085g, Apr. 10, 1996.
Product label for Tab–Let product (Danish, English); Distributed in Denmark at least as early as May 1996.
Advertisement for Tab–Let (Danish, English); Denmark's Big Coupon Catalog, Jun. 1996.
Advertisement for Tab–Let (Danish); Danish Newspaper "Ugebladet For Møn," week 21, vol. 11, May 26, 1996.
Biography: Dr. Lasse Lief Hessel M.D.; Femi–X™ product promotion, 2004, web publication: http://www.femi-x.com /page.php?x=hessel.
Bateman, D.N., et al.; Measurement of gastric emptying by real–time ultrasound; 1982 Gut. 23: 524–727.
Holt, S., et al.; Dynamic imaging of the stomach by real–time ultrasound—a method for the study of gastric motility; 1980, Gut., 21: 597–601.
Olefsky, J.M.; Obesity; 1994, Harrington's Principles of Internal Medicine, 446–452.
Ministry of Industry, Directory of Patents, Denmark; Reply to letter of Jan. 12, 1996, Oct. 4, 1996.
The Eurasian Patent Organization, The Eurasian Patent Office; Conclusion on Patentability of Invention, Oct. 10, 2001.
Patent Institute of Turkey; Citations and Explanations, Sep. 16, 2003.

* cited by examiner

*Primary Examiner*—Brenda Brumback

(57) ABSTRACT

Compositions containing a combination of selected herbal plant extracts that inhibit gastric emptying time and increase metabolic rate are provided which are useful in reducing weight in patients.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–3 are cancelled.

* * * * *